United States Patent [19]

Saito et al.

[11] Patent Number: 5,034,476
[45] Date of Patent: Jul. 23, 1991

[54] SURFACE-TREATED POLYORGANOSILSESQUIOXANE FINE POWDER

[75] Inventors: Kenji Saito; Hiroshi Kimura, both of Gunma, Japan

[73] Assignee: Toshiba Silicone Co., Ltd., Tokyo, Japan

[21] Appl. No.: 340,209

[22] Filed: Apr. 19, 1989

[30] Foreign Application Priority Data

Apr. 19, 1988 [JP] Japan .................................. 63-94549

[51] Int. Cl.$^5$ ............................................. C08L 83/12
[52] U.S. Cl. ................................... 525/477; 428/407; 428/447
[58] Field of Search ................. 525/477; 428/407, 447

[56] References Cited

U.S. PATENT DOCUMENTS

| 3,318,844 | 5/1967 | Krantz | 525/477 |
| 4,528,390 | 7/1985 | Kimura | 556/450 |
| 4,871,616 | 10/1989 | Kimura et al. | 428/407 |
| 4,895,914 | 1/1990 | Saitoh et al. | 525/478 |

FOREIGN PATENT DOCUMENTS 63-017958  1/1988  Japan .................................. 525/477

Primary Examiner—John C. Bleutge
Assistant Examiner—R. Dean, Jr.
Attorney, Agent, or Firm—Sughrue, Mion, Zinn, Macpeak & Seas

[57] ABSTRACT

A polyorganosilsesquinoxane fine powder having a moderate hydrophilicity, which is surface-treated with a block- or graft-copolymer comprising a polyoxyalkylene segment and a polysiloxane segment.

3 Claims, No Drawings

SURFACE-TREATED POLYORGANOSILSESQUIOXANE FINE POWDER

FIELD OF THE INVENTION

This invention relates to a surface-treated polyorganosilsesquioxane fine powder having a moderate hydrophilicity.

BACKGROUND OF THE INVENTION

It is well known that polymethylsilsesquioxane is a polymer comprising methylsilsesquioxane units which are a trifunctional organosilicon unit, and can take a fine powder form. One of the present inventors previously found a method for the preparation of a polymethylsilsesquioxane fine powder suitable as a material for electronic parts and an additive for polymers as disclosed in, for example, JP-A-63-77940 and 63-295637 (The term "JP-A" as used herein means an "unexamined published Japanese patent application").

The silicone resin fine powder comprising methylsilsesquioxane units obtained by such a method is composed of minute spherical particles usually having a particle diameter of about 0.05 to 100 μm, and has advantages over silica in having a smaller specific gravity and better slip properties and being excellent in dispersibility into organic resins and organic liquids.

However, since the polymethylsilsesquioxane fine powder is hydrophobic, it has been desired for the fine powder to have moderate hydrophilicity and affinity while having a small specific gravity and good slip properties which are the inherent characteristic of the polymethylsilsesquioxane fine powder.

As an example of treatment of an inorganic powder with a polyoxyalkylene-polysiloxane copolymer, a method for preventing development of microgrits by using titanium dioxide treated with such a copolymer, as a component of a treating agent for resin-coated paper for use in photographic printing is known as disclosed in, for example, JP-A-62-25753. However, no example of the treatment with above-described copolymer of a polyorganosilsesquioxane fine powder is yet known.

SUMMARY OF THE INVENTION

Accordingly, an object of the present invention is to provide a surface-treated polyorganosilsesquioxane fine powder having moderate hydrophilicity.

DETAILED DESCRIPTION OF THE INVENTION

The present inventors have found that a novel fine powder of polyorganosilsesquioxane which has been surface-treated with a copolymer of a polyoxyalkylene and a polysiloxane shows not only a small specific gravity and good slip properties but also moderate hydrophilicity, and that this novel fine powder is useful as a material for cosmetics, etc. The present invention is based on these findings.

The polyorganosilsesqioxane fine powder of the present invention is a polyorganosilsesquioxane fine powder which is surface-treated with a block- or graftcopolymer comprising a polyoxyalkylene segment and a polysiloxane segment.

The polyorganosilsesquioxane which can be used in this invention is represented by the formula: $[RSiO_{3/2}]p$ wherein R represents s substituted or unsubstituted monovalent hydrocarbon group, and p is a number which is sufficient for the polymer to be solid.

Examples of the group R include an alkyl group such as methyl, ethyl, propyl, butyl, pentyl, hexyl, heptyl, octyl, nonyl, decyl or dodecyl; a cycloalkyl group such as cyclopentyl or cyclohexyl; an aralkyl group such as 2-phenylethyl or 2-phenylpropyl; an aryl group such as phenyl or tolyl; an alkenyl group such as vinyl or allyl; and a substituted hydrocarbon group such as γ-chloropropyl, γ-methaorYloxypropyl, γ-glycidoxypropyl or 3,4-epoxycyclohexylethyl. Of those, methyl and phenyl are preferred, since the polyorganosilsesquioxane in which R is methyl or phenyl can be easily synthesized and the final fine powder of such a polymer is excellent in heat resistance. Further, methyl is more preferred in that a polyorganosilsesquioxane fine powder having a desired average particle diameter can be obtained because control of particle diameter is easy.

The average particle diameter of the polyorganosilsesquioxane is not especially limited. However, from the standpoint of the stability of a liquid disperse system in the case of dispersing the fine powder of this invention into the liquid phase, it is preferably 100 μm or less, more preferably in the range of from 0.05 to 20 μm.

Such a polyorganosilsesquioxane fine powder can be prepared by, for example, the method described in JP-A-60-13813.

The invention relates to a process for the preparation of polymethylsilsequioxane, characterized in that a methyltrialkoxysilane or its partially hydrolyzed condensate is hydrolyzed and condensed in an aqueous solution of ammonia or an amine.

Methyltrialkoxysilanes or their partially hydrolyzed condensates which are used as starting materials according to the present invention may be obtained by alkoxylation of methyltrichlorosilane with suitable alcohols according to conventional processes.

The chlorine content of a methyltrialkoxysilane or its partially hydrolyzed condensate which is due to hydrogen chloride by-product or unhydrolyzed methylchlorosilane is not critical.

In the invention, ammonia or amines serve to neutralize chlorine atoms which remain in the alkoxylation product, and act as a catalyst for the hydrolysis and condensation off the methyltrialkoxysilane. Examples of suitable amines include monomethylamine, dimethylamine, monoethylamine, diethylamine and ethylenediamine.

Ammonia is preferred, since it is less toxic and inexpensive, and can be readily removed. Generally, a commercially available aqueous ammonia solution (concentration: 28%) is used.

The amount of ammonia or amine used must be sufficient to neutralize chlorine atoms present in the alkoxysilane or its partially hydrolyzed condensate as described above and to catalyze the hydrolysis and condensation.

The amount of an aqueous solution of ammonia or amine used must be sufficient to account for more than twice the stoichiometric amount of water required to hydrolyze the alkoxy groups of the alkoxysilane or its partially hydrolyzed condensate described above and the chlorine atoms of unreacted chlorosilane.

The hydrolysis and condensation reaction can be conducted by dropwise addition of a methyltrialkoxysilane to an aqueous solution of ammonia or an amine under stirring. Upon stirring for several hours after the addition, the desired product is obtained. Preferably the hydrolysis-condensation reaction is conducted under heating, since the reaction time can thereby be reduced to obtain the desired product more readily.

Generally the temperature may be the reflux temperature of the reaction mixture. The reaction time is 1 to 2 hours at 70° to 90° C.

When the reaction is conducted under the conditions as described above, a precipitate of polymethylsilsequioxane separates out as the reaction proceeds. The precipitate is collected, washed with water and dried to give the desired powder product having an improved flow property and good compatibility with synthetic resins.

The block- or graft-copolymer used as a surface-treating agent is a straight chain or branched copolymer comprising a polyoxyalkylene segment and a polysiloxane segment. This copolymer may be a block-copolymer, a graft-copolymer with a polysiloxane segment as its main chain, or a graft-copolymer with a polyoxyalkylene segment as its main chain. Further, it may also be a graft-polymer comprising a block-terpolymer main chain and polyoxyalkylene segments grafted thereto, the main chain primarily comprising polysiloxane segments.

In such block- or graft-copolymers, the bonding between a polyoxyalkylene segment and a polysiloxane segment may be made through an Si-O-C bond. However, since the Si—O—C bond is susceptible to hydrolysis, it is preferred from the standpoint of lasting stability that a methylene group, a trimethylene group, a tetramethylene group, $-(CH_2)_3CO-$, $-3(CH_2)_3OCH_2CH(OH)CH_2-$ or the like should be present between the silicon atom and the oxygen atom. Of such groups, a trimethylene group is particularly preferred because of easy synthesis of the polymer.

Examples of the oxyalkylene units constituting the polyoxyalkylene segment are an oxyethylene unit, an oxypropylene unit, an oxytrimethylene unit, an oxytetramethylene unit, etc. The polyoxyalkylene segment may comprise units of one or more kinds selected from the above-described examples.

In order to impart moderate hydrophilicity to the final surface-treated fine powder, it is preferred that the polyoxyalkylene segment be a polyoxyethylene segment or a random- or block-copolymer segment comprising oxyethylene units and oxypropylene units. Examples of the end group of the polyoxyalkylene segment are hydroxyl; an alkoxy group such as methoxy, ethoxy or butoxy; etc.

In the polysiloxane segment, examples of the organic groups bonded to silicon atoms include an alkyl group such as methyl, ethyl, propyl, butyl, pentyl or hexyl; an alkenyl group such as vinyl or allyl; an aryl group such as phenyl; and a substituted hydrocarbon group such as γ-chloropropyl or γ-aminopropyl. Organic groups of one or more kinds selected from such examples may be bonded to the silicon atoms.

The average molecular weight of the block- or graft-copolymer is not especially limited, but is preferably in the range of from 1,000 to 20,000, because a copolymer with such average molecular weight has a good treating effect and can be easily handled. In the case of a graft-copolymer with a polysiloxane segment as its main chain, it is preferred that the number of siloxane units to which polyoxyalkylene segments are bonded be from 1 to 10 and the number of the other siloxane units be from 5 to 60.

For the surface treatement of the polyorganosilsesquioxane fine powder with the block- or graft-copolymer, any method can be employed so long as the surfaces of the fine powder can be covered with the copolymer. For example, the following methods can be employed: a method in which the fine powder is placed in the copolymer, thereby allowing the copolymer to be adsorbed onto the fine powder; a method in which a mixture of the fine powder and the copolymer is ground by means of a ball mill, a mortar or the like, to perform surface treatment; a method in which a solution of the copolymer is prepared using a solvent capable of dissolving the copolymer and the fine powder is then added thereto, thereby allowing the copolymer to be adsorbed onto the fine powder; and a method in which the fine powder is dispersed into a solvent capable of dissolving the copolymer and the copolymer is then added thereto, thereby allowing the copolymer to be adsorbed onto the fine powder. Examples of the solvent are water, methanol, ethanol, ethylene glycol and the like, and a suitable solvent can be selected according to the solubility of the copolymer and the purpose of use of the final treated fine powder. The solvent which has been used in the treatment may be or may not be removed depending upon the purpose of use of the final product.

The amount of the block- or graft-copolymer used in the surface treatment varies depending upon the specific surface area of the fine powder, but is generally from 1 to 30 wt% based on the weight of the fine powder.

The surface-treated polyorganosilsesquioxane fine powder of this invention not only has a small specific gravity and good slip properties but also is excellent in hydrophilicity and affinity, and has active surfaces.

The fine powder of the present invention is extremely useful as a component of cosmetics, an active ingredient for antiformers, a component of strippable coating compositions, a wetting agent, and a dispersed phase in electroviscous liquids.

The present invention will be explained in more detail by reference to the following Examples and Comparative Examples, which should not be construed as limiting the scope of the invention. In these examples, all parts are by weight unless otherwise indicated.

In the Examples, surface-treating agents, F-1 to F-4, each having the following average molecular structure, were used. In the structural formulae F-1 to F-3, the siloxane units of plural kinds do not particularly mean a block structure.

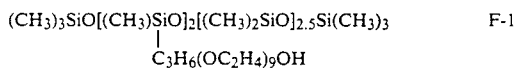

F-1

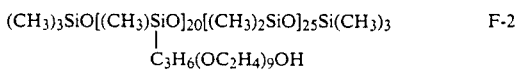

F-2

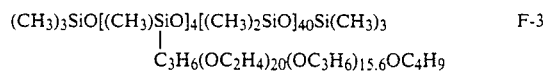

F-3

F-4

EXAMPLE 1

According to the method described in JP-A-60-13813, methyltrimethoxysilane was brought into contact with an aqueous solution of ammonia to obtain a polymethylsilsesquioxane fine powder having an average particle diameter of 2 μm. 100 Parts of the thus-obtained fine powder was introduced into an automatic mortar. 6 Parts of F-1 and 10 parts of water were added thereto, and the resulting mixture was stirred at room temperature for 2 hours. Thus, a surface-treated polymethylsilsesquioxane fine powder was obtained in which F-1 had been uniformly adsorbed onto the surfaces of the polymethylsilsesquioxane fine powder.

In more detail; to a 1 liter four-necked flask fitted with a thermometer, a reflux condenser and a stirrer were charged 500 parts of water and 50 parts of a 28% aqueous solution of ammonia. 200 parts of methyltrimethoxysilane containing 5 ppm (in terms of chlorine atom) methyltrichlorosilane was added dropwise to the flask over 40 minutes while stirring. The reaction temperature was 10° C. At the beginning, and reached 30° C. at the end of the addition. The mixture was refluxed at 84° C. by a mantle heater for about an hour. After cooling the mixture, a precipitated product was collected, washed with water and dried to obtain polymethylsilsesquioxane powder having improved flow property. The product contained not more than 0.1 ppm of chlorine atom.

The stability of a disperse system when the thus-obtained surface-treated polymethylsilsesquioxane fine powder was dispersed into a liquid phase was evaluated by a sedimentation test as follows.

That is, 25 parts of the surface-treated polymethylsilsesquioxane fine powder was dispersed into 75 parts of dimethyl silicone oil having a viscosity as measured at 25° C of 20 cSt, to prepare a liquid dispersion. This dispersion was introduced into a cylindrical vessel made of glass, and allowed to stand at 25° C. for 240 hours. Thereafter, the height ($h_1$) of a supernatant transparent layer which had resulted from sedimentation of the fine powder and the height ($h_2$) of the lower suspension layer were measured. From these values, a sedimentation degree was obtained using the following equation.

Sedimentation degree = $h_1/(h_1+h_2)$

It should be noted that the lower the sedimentation degree, the stabler the disperse system. The result obtained is shown in Table 1.

EXAMPLES 2 TO 5

The same procedures as in Example 1 were repeated except that the surface-treating agents as shown in Table 1 were used in place of F-1, thereby obtaining surface-treated polymethylsilsesquioxane fine powders. With respect to each of the thus-obtained surface-treated fine powders, a sedimentation degree was obtained in the same manner as in Example 1. The results obtained are shown in Table 1.

COMPARATIVE EXAMPLE

A polymethylsilsesquioxane fine powder which had not been surface-treated and having an average particle diameter of 2 μm was tested for sedimentation degree, in the same manner as in Example 1. The result obtained is shown in Table 1 below.

TABLE 1

| | Surface-treating agent (part) | | | | Sedimentation |
|---|---|---|---|---|---|
| | F-1 | F-2 | F-3 | F-4 | degree |
| Example 1 | 6 | — | — | — | 0.02 |
| Example 2 | — | 6 | — | — | 0.01 |
| Example 3 | — | — | 6 | — | 0.05 |
| Example 4 | 6 | — | — | 3 | 0.03 |
| Example 5 | 20 | — | — | — | 0.01 |
| Comparative Example | — | — | — | — | 0.15 |

While the invention has been described in detail and with reference to specific embodiments thereof, it will be apparent to one skilled in the art that various changes and modifications can be made therein without departing from the spirit and scope thereof.

What is claimed is:

1. A polyorganosilsesquioxane fine powder which is surface-treated with a block- or graft-copolymer comprising a polyoxyalkylene segment and a polysiloxane segment.

2. The polyorganosilsesquioxane fine powder as claimed in claim 1, wherein the fine powder is represented by the formula $[RSiO_{3/2}]p$ wherein R represents a substituted or unsubstituted monovalent hydrocarbon group, and p is the number which is sufficient for the fine powder to be solid.

3. The polyorganosilsesquioxane fine powder as claimed in claim 1, wherein the fine powder has an average particle diameter of 100 μm or less.

* * * * *